United States Patent
Koh et al.

[11] Patent Number: 6,059,937
[45] Date of Patent: May 9, 2000

[54] SENSOR HAVING TIN OXIDE THIN FILM FOR DETECTING METHANE GAS AND PROPANE GAS, AND PROCESS FOR MANUFACTURING THEREOF

[75] Inventors: Seok Keun Koh; Hyung Jin Jung; Seok Kyun Song; Won Kook Choi, all of Seoul; Dongsoo Choi; Jin Seok Jeon, both of Ansan, all of Rep. of Korea

[73] Assignee: Korea Gas Corporation, Seoul, Rep. of Korea

[21] Appl. No.: 08/654,055

[22] Filed: May 28, 1996

[30] Foreign Application Priority Data

Dec. 22, 1995 [KR] Rep. of Korea .................. 95/54969

[51] Int. Cl.[7] .................. C23C 14/34; C23C 14/08
[52] U.S. Cl. .................. 204/192.11; 204/192.15; 204/192.23; 204/192.29; 427/126.3; 427/527; 427/529; 427/531; 427/563; 427/564; 427/576; 427/584
[58] Field of Search .................. 204/192.11, 192.15, 204/192.26, 192.23, 192.25, 192.29; 427/77, 78, 126.3, 523, 527, 529, 531, 562, 563, 564, 576, 584

[56] References Cited

U.S. PATENT DOCUMENTS

| | | | |
|---|---|---|---|
| 3,479,257 | 11/1969 | Shaver | 436/144 |
| 4,142,958 | 3/1979 | Wei et al. | 204/192.11 |
| 4,313,338 | 2/1982 | Abe et al. | 73/31.06 |
| 4,714,631 | 12/1987 | Aufderheide | 427/250 |
| 5,003,812 | 4/1991 | Yagawara et al. | 73/31.06 |
| 5,250,170 | 10/1993 | Yagawara et al. | 204/431 |
| 5,605,612 | 2/1997 | Park et al. | 204/429 |

FOREIGN PATENT DOCUMENTS

| | | | |
|---|---|---|---|
| 62-216112 | 9/1987 | Japan | 427/531 |
| 5-171437 | 7/1993 | Japan | 204/192.11 |

OTHER PUBLICATIONS

Kim, *Gas Sensors and Application Thereof*, p. 6, 1993.
Fukui et al., *Sensors and Actuators B*, 13–14:589–590, 1993.
Dutronc et al., *Sensors and Actuators B*, 15–16:24–31, 1993.
Koh et al., *Journal of Vacuum Science and Technology A*, 13:2123–2127, 1995.

*Primary Examiner*—Rodney McDonald
*Attorney, Agent, or Firm*—Darby & Darby

[57] ABSTRACT

The present invention relates to a sensor for detecting hydrocarbon type gas such as methane gas and propane gas, and process for manufacturing thereof. $SiO_2$ was deposited in 1 $\mu$m by ion beam sputtering with a mixed gas (3:2) of argon and oxygen on a silicon wafer in the process. In case of a propane sensor, platinum electrode is deposited in 600 Å by ion beam sputtering on a tin oxide thin film synthesized by ionized beam of which the oxygen ion energy is 0 to 500 eV by using poly alumina. In case of a methane sensor, heat treatment at 500° C. was performed for 1 hour in the air in order for the thin film to be stable at high operation temperature, while heat treatment was not performed in case of propane sensor. The sensor was manufactured by adding platinum or palladium thereto by argon ion beam sputtering. The thin film type tin oxide sensor according to the present invention exhibited an excellent selectivity of 47.4% even at low temperature of 150° C. at a gas concentration of 3,000 ppm in case of the methane sensor, while a sensor having high electric sensitivity and selectivity as 93.4% was obtained in case of the propane sensor.

9 Claims, 4 Drawing Sheets

SENSOR HAVING TIN OXIDE THIN FILM FOR DETECTING METHANE GAS AND PROPANE GAS, AND PROCESS FOR MANUFACTURING THEREOF

BACKGROUND OF THE INVENTION

1. Field of the Invention

The present invention relates to a sensor for detecting methane gas and propane gas, which has tin oxide ($SnO_2$) thin film instead of thick film or bulk type of tin oxide conventionally used for detecting reductive inflammable gas [e.g. propane ($C_3H_8$), butane ($C_4H_{10}$)], and which can detect methane or propane gas at very low temperature.

2. Description of the Conventional Art

Generally, methane gas has lower specific gravity (0.554) than propane(1.52) or butane gas(2.00). As methane gas is lighter than the air, it rises to the upper side of the room when it is leaked. Also, it is less explosive than other gases as the explosive minimum concentration of methane gas (5.00%) is higher than other gases (propane: 2.12%/butane: 1.80%) [KIM, Young Hae, Gas Sensors and Application thereof, Kijeon-Younku-Sa, 1993, p.6].

In these circumstances, researches for applying methane gas as fuel are increasingly performed recently in order to develop a stable and clean fuel. Thus, a development of a sensor for detecting the leakage of methane gas as mentioned above and of propane gas which is widely used as fuel is urgently requested.

As conventional sensors for gas detection have had a type of bulk or thick film rather than thin film, gas sensitivity was lower than that of a thin film type sensor, and was disadvantageous in that production in large scale was difficult owing to hand-working, to cause high price of the product.

As a sensor for inflammable gas presently used in Korea, a bulk type sensor based on $SnO_2$ imported from Japan may be mentioned. However, it is disadvantageous in that it requires much labor for its mass production and has low selectivity, while a process of heat treatment at high temperature must be involved in its production.

Meanwhile, as the conventional methane sensors and propane sensors have very high operation temperature (more than 400° C. and more than 300° C., respectively) to cause high electric power consumption, and a selective sensor has not yet been disclosed because methane gas has a stable chemical structure [Kiyoshi Fukui and Masanori Nakane, Effects of oxide semiconductor-electrode interface on gas-sensitivity characteristics, Sensors and Actuators B, 15–16 (1993), 24–31].

Because of the difficulties of selecting a sensor for detecting methane gas, a method for indirectly estimating the presence of methane gas by combining two or more sensors has been reported [Pascale Durone et al., A new approach to selectivity in methane sensing, Sensors and Actuators B, 15–16(1993), 24–31]. However, this method is an indirect estimating method and requires a complicated electronic device owing to the use of two or more sensors.

On the other hand, a sensor of thin film type having a thickness of several hundreds to several thousands Å may result in improved sensitivity, reproductivity and mass productivity as well as minimizing electric power consumption by virtue of miniaturization, whereby lowering the price. Up to the present, however, any research or invention with regard to a thin film type sensor which can provide sufficient selectivity to be applied to detection of methane or propane gas has not been reported.

Recent studies are focused to an addition of rare element such as platinum or palladium to a prepared thin film in order to increase the sensitivity of $SnO_2$ sensor. Though developments of a novel process for preparing thin film to which rare element can be easily added are intended, it has not yet been developed inside or outside the country. This is because most of the researches tried to prepare the thin film by physical sputtering or chemical vapor deposition, by which controlling of the thickness, orientation, crystallinity, density or ultrafine processing is unable or very difficult in practice.

In the preparation of the thin film type sensor, a method using ion beam is known to be able to afford a thin film having high quality and high density during the low temperature process through all kinds of metals, semiconductors and oxides [S. K. Koh et al., Effects of Residual Gas on Cu Film Deposition by Partially Ionized Beam, JVST-A, 13(4), 1995, 2123–2127].

According to the present invention, $SnO_2$ thin film can be formed at room temperature by vaporizing neutral Sn metal by the use of metal gun, with ionizing oxygen ($O_2^{30}$) by the use of a gas ionized gun, and applying energy thereto.

The principles and characteristics of the gas ion source mentioned above is suggested in a disclosed article of the present inventors [S. K. Koh et al., Characteristics of a Metal Ion Source for Fabricating Sn Metal in an $O_2$ Environment, Ungyong Mulli, 9(2), 1996, 246–252.

SUMMARY OF THE INVENTION

The object of the present invention is to provide a sensor for detecting methane gas, constructed by forming $SiO_2$ insulating layer on the upper side of Si base plate; depositing $SnO_2$ thin film on the upper side of the $SiO_2$ insulating layer; forming a platinum electrode on the upper side of the $SnO_2$ thin film; and doping platinum or palladium on the upper side. A thin film is defined as a film having a thickness of less than 1 $\mu$m.

The sensor for detecting methane gas according to the present invention has a simple structure by virtue of its high selectivity and low operation temperature, and has a long life span so that it can be applied as an excellent sensor for detecting methane gas.

Another object of the present invention is to provide a process for manufacturing a methane sensor using tin oxide thin film, comprising the steps of depositing $SiO_2$ with a mixed gas of argon and oxygen on Si base plate by using ion beam sputtering;

vaporizing Sn metal with ionized oxygen, and depositing $SnO_2$ thin film on the $SiO_2$ by applying energy to the ionized oxygen;

depositing a platinum electrode on the $SnO_2$ thin film by ion beam sputtering;

heat treating thereof at a predetermined temperature in the air; and doping platinum or palladium by argon ion beam sputtering.

Still another object of the present invention is to provide a sensor for detecting propane gas, which is constructed by depositing $SnO_2$ thin film on the upper side of poly alumina base plate; forming a platinum electrode on the upper side of the $SnO_2$ thin film; and doping palladium on the upper side thereof.

Another object of the present invention is to provide a process for manufacturing a propane sensor using tin oxide thin film, comprising the steps of vaporizing Sn metal with ionized oxygen, and applying energy to the ionized oxygen to deposit $SnO_2$ thin film on a poly alumina base plate;

depositing a platinum electrode on the $SnO_2$ thin film by ion beam sputtering; and adding palladium thereto by argon ion beam sputtering.

DETAILED DESCRIPTION OF THE INVENTION

Here-in-after, the present invention is described in more detail.

According to an embodiment to manufacture a thin film type tin oxide sensor of the present invention, as a base plate, $SiO_2$ was deposited in 1 μm by ion beam sputtering with a mixed gas (3:2) of argon and oxygen on Si(100) in case of methane sensor, while poly alumina was used in case of propane sensor.

To the base plate, tin oxide thin film was synthesized by ion beam of which the oxygen ion energy was 0 to 500 eV and deposited, and platinum electrode was deposited thereto in 600 Å by ion beam sputtering. In case of a methane sensor, heat treatment at 500° C. was performed for 1 hour in the air in order for the thin film to be stable at high operation temperature, while heat treatment was not performed in case of propane sensor.

The sensor manufactured by doping platinum or palladium thereto by argon ion beam sputtering exhibited an excellent selectivity of 47.4% (much higher than that of propane, 8.1%) even at low temperature of 150° C. at a gas concentration of 3,000 ppm in case of the methane sensor. A sensor having high electric sensitivity and selectivity as 93.4% was obtained in case of the propane sensor.

The gas sensitivity measured in the experiments of the present invention is defined as the following equation:

$$\text{Sensitivity (\%)} = \frac{R_a - R_g}{R_a} \times 100$$

wherein, $R_a$ is electric resistance of the sensor in the air, and $R_g$ is electric resistance of the sensor in the gas.

DETAILED DESCRIPTION OF PREFERRED EMBODIMENT

Now, the present invention is described by referring to the figures attached.

Figure 1A:
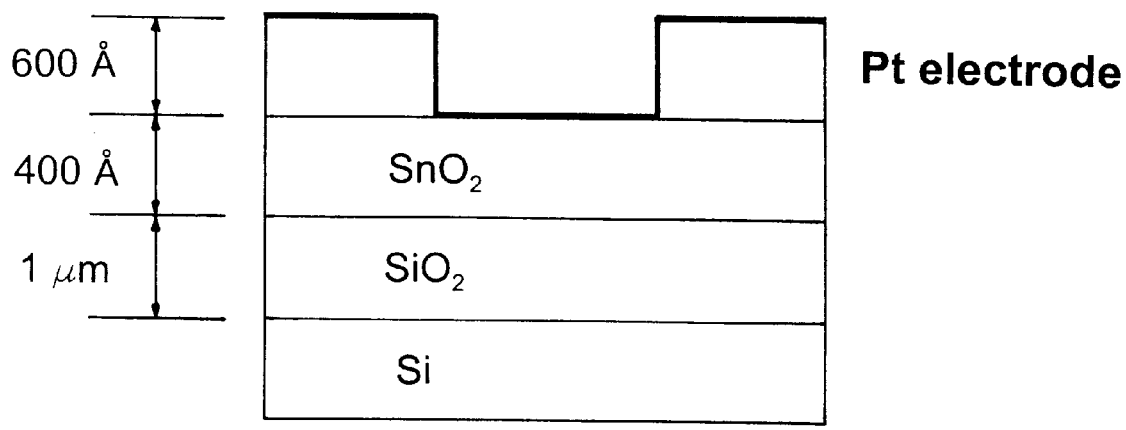
FIG. 1(A) is a outlined sectional view of a sensor for detecting methane gas.
Figure 1B:
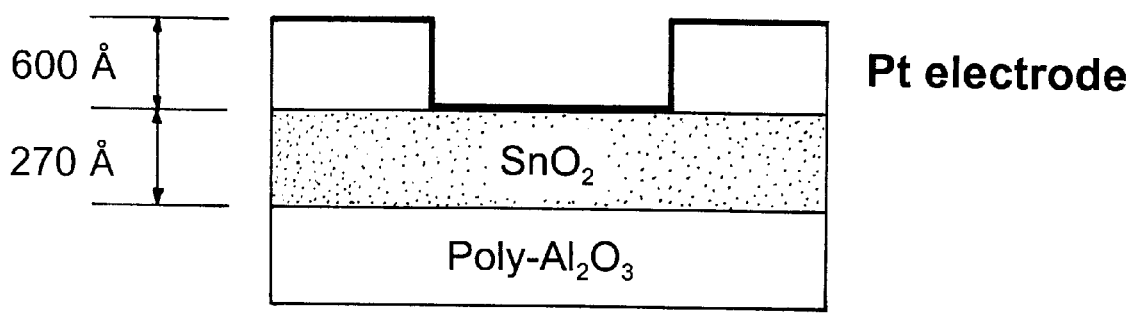
FIG. 1(B) is a outlined sectional view of a sensor for detecting propane gas.

FIG. 1(A) is a sectional view of a sensor for detecting methane gas, and FIG. 1(B) is that for detecting propane gas. Tin oxide thin film was prepared in 400 Å by hybrid ion beam in which tin metal was deposited with an ionized cluster beam source on a silicon wafer having 1 μm of $SiO_2$ insulating layer while simultaneously irradiating oxygen ion($O_2^+$) of which ion beam potential is 0 eV with ion current density of 1.71 μA/cm².

An electrode was formed by depositing platinum in 600 Å by using ion beam sputtering thereto. After heat treatment at 500° C. in the air for 1 hour, platinum was doped in 105 Å by ion beam sputtering, and heat treatment was performed at 500 ° C. in the air for 30 minutes for internal diffusion of platinum.

Figure 2:
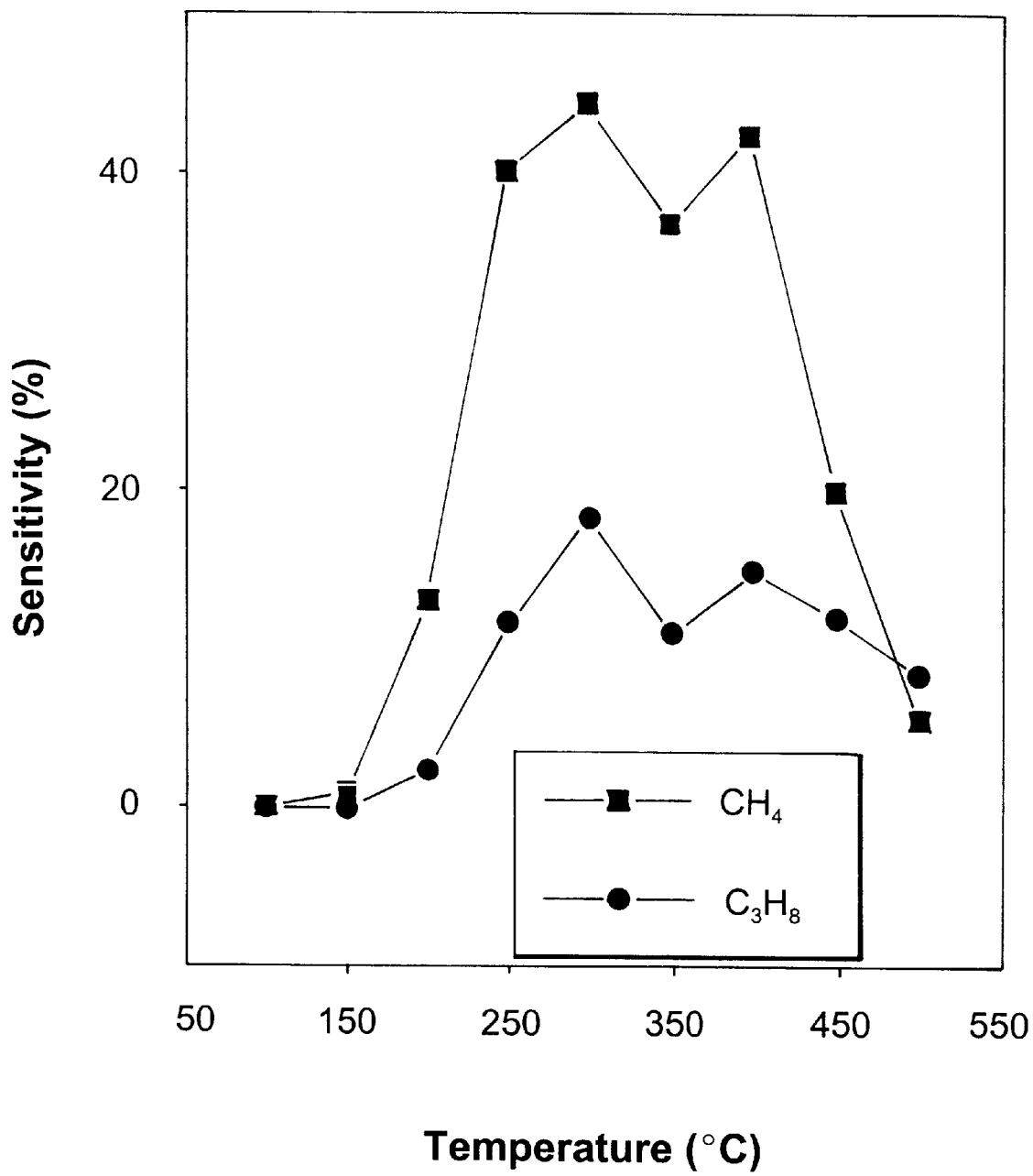
FIG. 2 is a graph showing the sensitivity properties of thin film prepared by adding 18 Å of platinum to tin oxide synthesized at 0 eV of oxygen ion beam energy, with respect to methane and propane at a concentration of 3000 ppm.

The electric sensitivity of the sensor thus obtained is shown in FIG. 2. As can be shown in the figure, the sensitivity of methane was higher than that of propane in the whole range of temperature. An appropriate operation temperature of the sensor is 250–300° C., and the selectivity of methane compared to propane at 250° C. and 300° C. are 3.43 folds and 2.43 folds, respectively.

Though the maximum sensitivity of methane at a relatively lower concentration of 3,000 ppm than its explosion minimum concentration of 50,000 ppm is low as 44.3%, there is no problem for the sensor to be used practically.

What are more important are excellent selectivity to methane and low operation temperature, and high sensitivity is secondly requested. In general, in case of methane gas, sensors exhibit no selectivity, and very low sensitivity as 10,000 to 20,000 ppm.

According to another embodiment of the present invention, tin oxide thin film was prepared in 400 Å by irradiating oxygen ion($O_2^{3o}$) of which ion beam potential is 300 eV with ion current density of 17.14 μA/cm². An electrode and heat treatment were performed in the example described above. Palladium was doped in 105 Å by ion beam sputtering. As different from the above example, heat treatment was not performed after the doping to reduce one step of the process.

Figure 3:
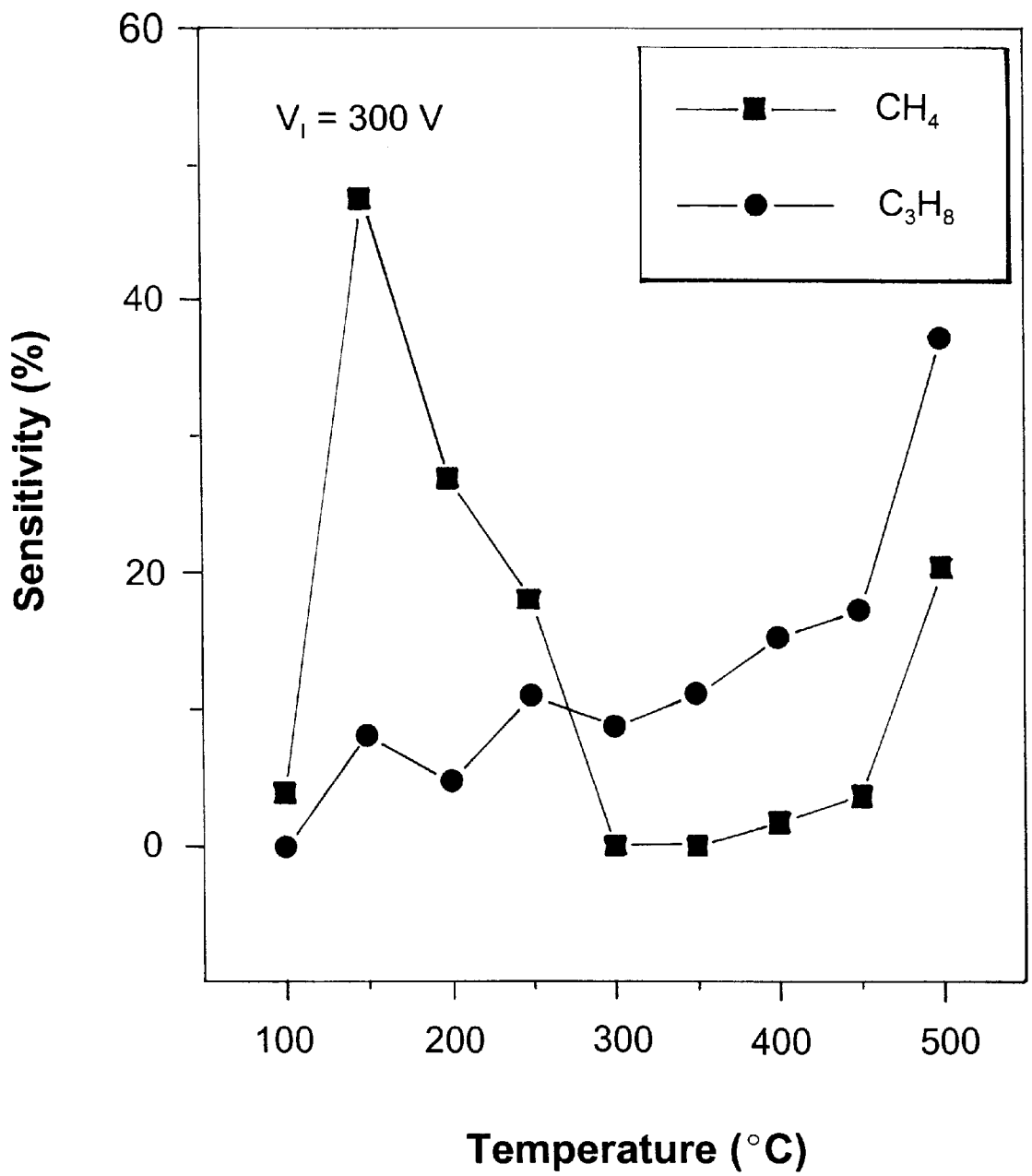
FIG. 3 is a graph showing the sensitivity properties of thin film prepared by adding 6 Å of palladium to tin oxide synthesized at 300 eV of oxygen ion beam energy, with respect to methane and propane at a concentration of 3000 ppm.

As can be shown in FIG. 3, very excellent properties against methane are exhibited at operation temperature of 150° C. In other words, the sensitivity of methane was very high as 47.4% (about 5.85 folds) as compared to that of propane, 8.1%, at a gas concentration of 3,000 ppm.

Figure 4:
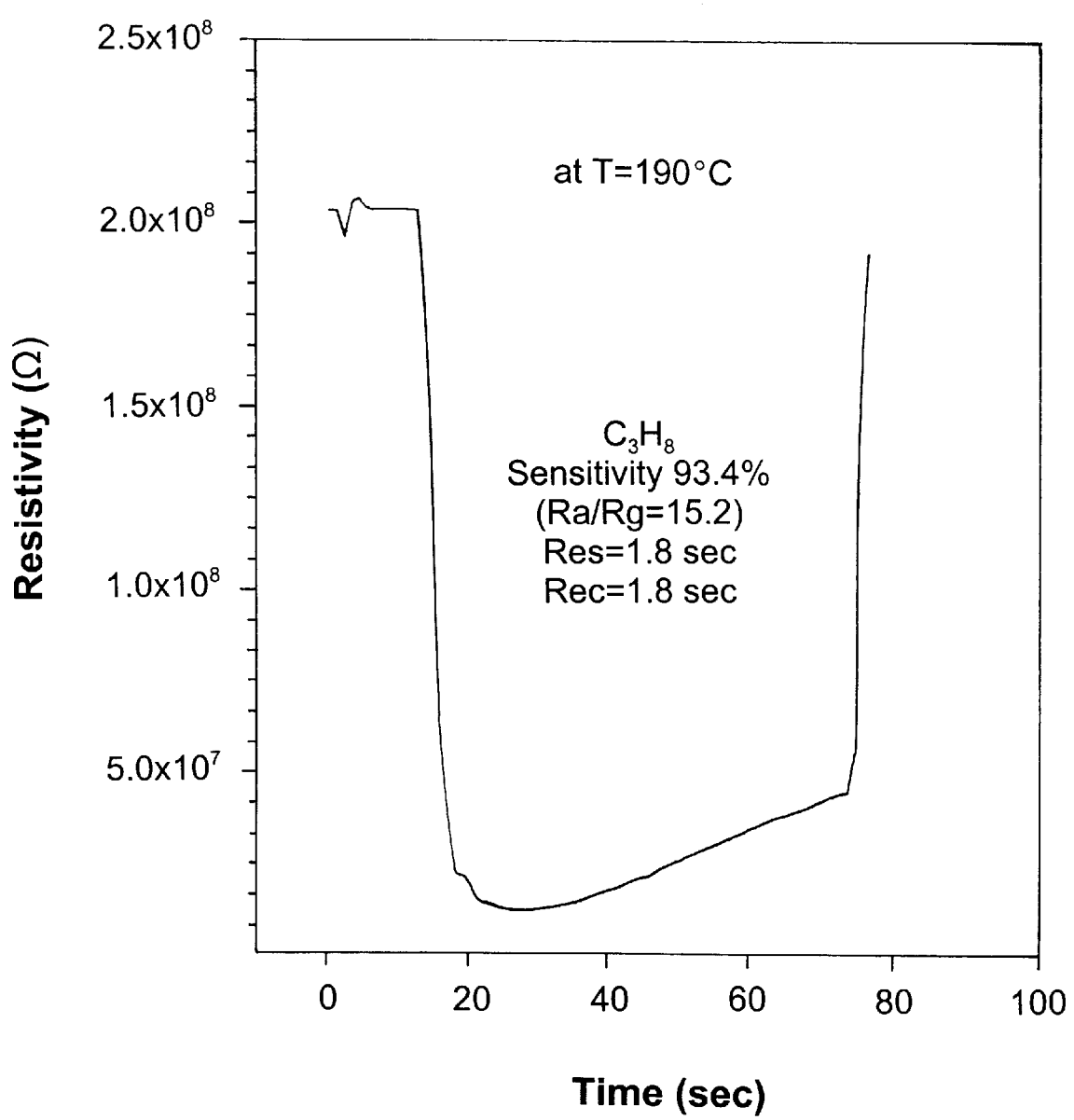
FIG. 4 is a graph showing the sensitivity and response properties of thin film prepared by adding 6 Å of palladium to tin oxide synthesized at 0 eV of oxygen ion beam energy and having $Al_2O_3$ base plate, with respect to propane gas at a concentration of 3000 ppm.

FIG. 4 shows electric sensitivity of the sensor for detecting propane gas. The structure is the same as FIG. 1(B). Using polycrystalline $Al_2O_3$ as a base plate, and tin oxide was formed in a thickness of 100–1000 Å by irradiating oxygen ion of 0 eV at room temperature with simultaneous vaporization of tin metal, and platinum is sputtered by ion beam to form an electrode of several hundreds Å. Finally, palladium was added on the surface in 105 Å, and heat treatment was not performed, whereby omitting 1–2 steps of the process to result in lowering the cost for production.

FIG. 4 shows the alterations of electric resistance of the sensor before and after the injection of propane gas at a sensor temperature of 190° C., and when it is reduced in the air. The resistance was $2 \times 10^8$ Ω in the air while $1.2 \times 10^6$ Ω (15.2 folds) at a propane gas concentration of 3,000 ppm. This results corresponds to 93.4% in accordance with the gas sensitivity equation described above, showing a very high value at low temperature, and the reaction time property is excellent as the response and recovering time with regard to the gas is total 1.8 sec.

Thus, the present invention provides an excellent sensor properties with regard to propane gas, and fine grains are formed by ion beam processing at the time of thin film growth. The catalytic activity due to palladium doping as a rare metal, optimum thickness, and surface roughness of 1 μm of $Al_2O_3$ base plate maximized the effects of the sensor. Therefore, the same results are expected in case of synthesizing $SnO_2$ thin film by using polycrystalline oxide having large surface roughness such as $Al_2O_3$ as a base plate.

As described above, the sensor using thin film prepared according to the present invention has very surprising performance which could not be expected in the conventional sensors, whereby the present invention is very useful in the art as even similar results have not yet been reported in the world.

What is claimed is:

1. A process for manufacturing a sensor for detecting methane gas using a tin oxide thin film, comprising the steps of
   (A) depositing $SiO_2$ with a mixed gas of argon and oxygen on a Si base plate by ion beam sputtering to form a $SiO_2$ layer;
   (B) synthesizing and depositing a $SnO_2$ thin film on the $SiO_2$ layer by using a hybrid ion beam from a metal ion gun and an oxygen gas ion gun; wherein the hybrid ion beam has an energy of from 0 to 500 eV;
   (C) depositing a platinum electrode on the $SnO_2$ thin film;
   (D) heat treating said platinum electrode at 500° C. in ambient atmospheric air; and
   (E) adding platinum or palladium to the $SnO_2$ thin film by ion beam sputtering to produce a metal catalyst.

2. A process for manufacturing a sensor for detecting methane gas using a tin oxide thin film according to claim 1, wherein the $SiO_2$ is deposited as an insulating layer of 1 μm.

3. A process for manufacturing a sensor for detecting methane gas using a tin oxide thin film according to claim 1, wherein the $SnO_2$ thin film is deposited at a thickness of 400 Å.

4. A process for manufacturing a sensor for detecting methane gas using a tin oxide thin film according to claim 1, wherein the platinum electrode is deposited at a thickness of 600 Å.

5. A process for manufacturing a sensor for detecting methane gas using a tin oxide thin film according to claim 1, wherein the heat treating is performed at 500° C. for 1 hour.

6. A process for manufacturing a sensor for detecting methane gas using a tin oxide thin film according to claim 1, wherein palladium or platinum is internally diffused during the adding of platinum or palladium to the $SnO_2$ thin film.

7. A process for manufacturing a sensor for detecting methane gas using a tin oxide thin film according to claim 6, wherein 105 Å of platinum is added as a doping metal by ion beam sputtering in step (E) and said heat treating is conducted at 500° C. for 30 minutes.

8. A process for manufacturing a sensor for detecting methane gas using a tin oxide thin film according to claim 1, wherein the palladium or platinum is added to the tin oxide thin film by ion beam sputtering after the heat treatment of the platinum electrode.

9. A process for manufacturing a sensor for detecting methane gas using a tin oxide thin film according to claim 8, wherein 105 Å of palladium is added as a doping metal by ion beam sputtering in step (E).

* * * * *